(12) United States Patent
Thalhammer et al.

(10) Patent No.: US 10,739,348 B2
(45) Date of Patent: Aug. 11, 2020

(54) CLUSTER FOR THE DETECTION OF AN ANALYTE

(71) Applicant: Helmholtz Zentrum München—Deutsches Forschungszentrum für Gesundheit und Umwelt (GmbH), Neuherberg (DE)

(72) Inventors: Stefan Thalhammer, Munich (DE); Elisângela Linares, Traunreut (DE)

(73) Assignee: HELMHOLTZ ZENTRUM MUNCHEN—DEUTSCHES FORSCHUNGSZE, Neuherberg (DE)

( * ) Notice: Subject to any disclaimer, the term of this patent is extended or adjusted under 35 U.S.C. 154(b) by 514 days.

(21) Appl. No.: 15/327,968

(22) PCT Filed: Aug. 6, 2015

(86) PCT No.: PCT/EP2015/068193
§ 371 (c)(1),
(2) Date: Jan. 20, 2017

(87) PCT Pub. No.: WO2016/020492
PCT Pub. Date: Feb. 11, 2016

(65) Prior Publication Data
US 2017/0212124 A1    Jul. 27, 2017

(30) Foreign Application Priority Data

Aug. 6, 2014   (EP) .................................. 14180042

(51) Int. Cl.
| | | |
|---|---|---|
| G01N 33/58 | (2006.01) | |
| G01N 33/533 | (2006.01) | |
| G01N 33/543 | (2006.01) | |
| B82Y 15/00 | (2011.01) | |
| G01N 33/558 | (2006.01) | |

(52) U.S. Cl.
CPC ......... *G01N 33/585* (2013.01); *G01N 33/533* (2013.01); *G01N 33/54313* (2013.01); *G01N 33/558* (2013.01); *G01N 33/582* (2013.01); *B01J 2219/005* (2013.01); *B01J 2219/00545* (2013.01); *B01J 2219/00576* (2013.01); *B82Y 15/00* (2013.01)

(58) Field of Classification Search
None
See application file for complete search history.

(56) References Cited

U.S. PATENT DOCUMENTS

2013/0234067 A1*   9/2013   Chiu et al. ............. B82Y 30/00
252/301.35

FOREIGN PATENT DOCUMENTS

| WO | WO 2007/070115 A1 | 6/2007 |
|---|---|---|
| WO | WO 2009/152209 A2 | 12/2009 |

OTHER PUBLICATIONS

Du et al. "Covalent coupling of organophosphorus hydrolase loaded quantum dots to carbon nanotube/Au nanocomposite for enhanced detection of methyl parathion" Biosensors and Bioelectronics 25 (2010) 1370-1375, with accompanying online Supplementary data, doi:10.1016/j.bios.2009.10.032.*
Gao et al. "Strongly Photoluminescent CdTe Nanocrystals by Proper Surface Modification" J. Phys. Chem. B, 1998, 102 (43), pp. 8360-8363, DOI: 10.1021/jp9823603.*
Li et al. "Nanoparticle-assisted DNA nanosensor", 2007 Asia Optical Fiber Communication and Optoelectronic Exposition and Conference, AOE, art. No. 4410711, pp. 84-86, DOI: 10.1109/AOE.2007.4410711.*
Powell et al., A Covalent Fluorescent-Gold Immunoprobe: Simultaneous Detection of a Pre-mRNA Splicing Factor by Light and Electron Microscopy, The Journal of Histochemistry & Cytochemistry, 1997, pp. 947-956, vol. 45(7).
Bai et al. "A sensitive lateral flow test strip based on silica nanoparticle/CdTe quantum dot composite reporter probes," RSC Advances, vol. 2, No. 1, (Jan. 1, 2012), p. 1778.
Chen et al."A Dual-Emission Fluorescent Nanocomplex of Gold-Cluster-Decorated Silica Particles for Live Cell Imaging of Highly Reactive Oxygen Species," Journal of The American Chemical Society, vol. 135, No. 31, (Aug. 7, 2013), pp. 11595-11602.
Draz et al. "Hybrid Nanocluster Plasmonic Resonator for Immunological Detection of Hepatitis B Virus," ACS NANO, vol. 6, No. 9, (Sep. 25, 2012), pp. 7634-7643.
Enriquez et al. "Enhanced resonance light scattering properties of gold nanoparticles due to cooperative binding," Analytical and Bioanalytical Chemistry, Springer, Berlin, DE, vol. 391, No. 3, (Feb. 15, 2008), pp. 307-815.
Nakanishi et al. "Versatile self-assembled hybrid systems with exotic structures and unique functions," Current Opinion in Colloid and Interface Science, London, GB, vol. 16, No. 6, (Aug. 28, 2011), pp. 482-490.
Tang et al. "Magnetic nanogold microspheres-based lateral-flow immunodipstick for rapid detection of aflatoxin B2 in food," Biosensors and Bioelectronics, Elsevier BV, NL, vol. 1, No. 2, (Oct. 15, 2009), pp. 514-518.

(Continued)

*Primary Examiner* — Christine Foster
(74) *Attorney, Agent, or Firm* — Pillsbury Winthrop Shaw Pittman LLP

(57) ABSTRACT

The present invention relates to a cluster for the detection of an analyte, said cluster comprising a plurality of visually detectable colored particles and a plurality of luminescent particles, wherein (i) the particles are bound to each other, and (ii) at least one binding partner of an analyte is bound to the colored particles and/or the luminescent particles.

Figure 1:
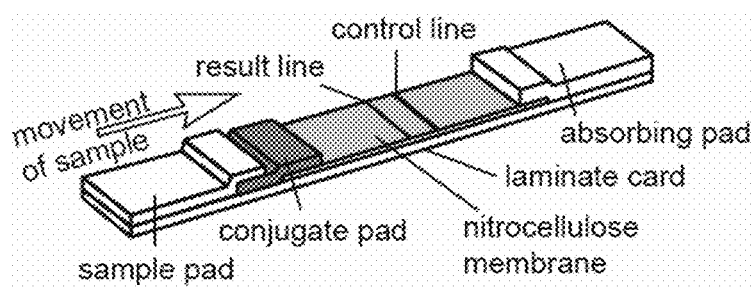
Figures 2A, 2B, 2C:
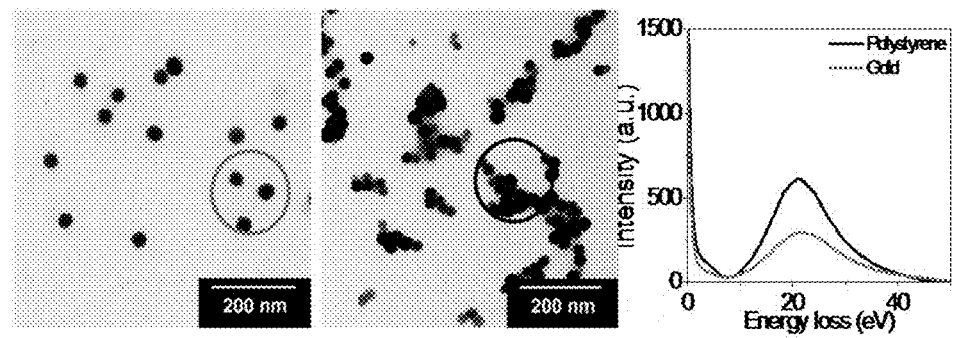
Figures 2D, 2E, 2F:
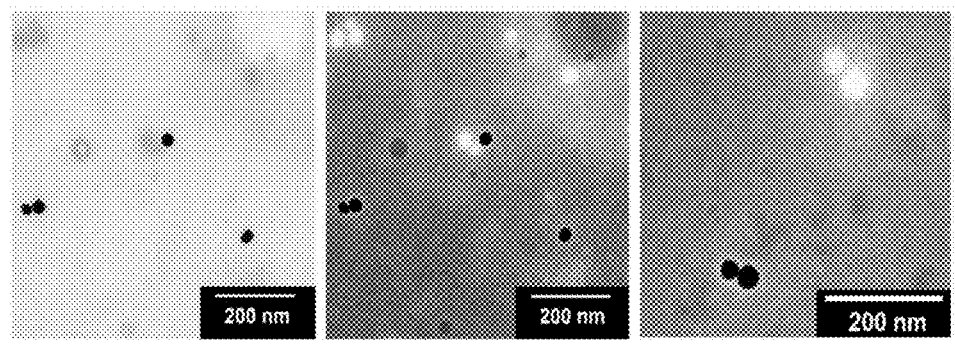
Figures 2G, 2H, 2I:
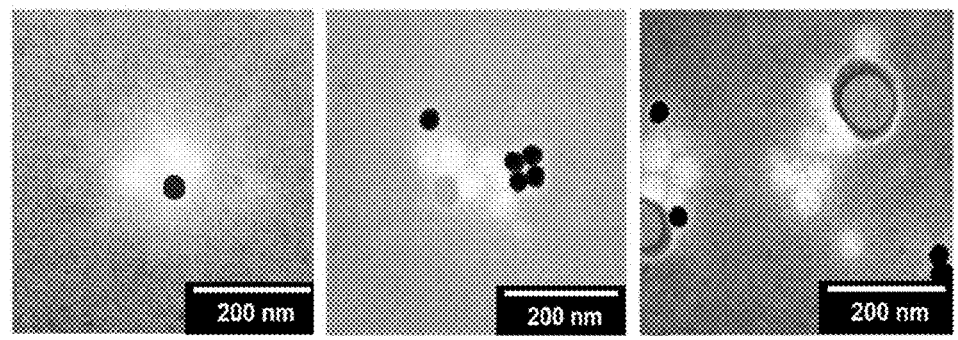

15 Claims, 3 Drawing Sheets
Specification includes a Sequence Listing.

(56) References Cited

OTHER PUBLICATIONS

Yao et al. "A novel method to prepare gold-nanoparticle-modified nanowires and their spectrum study," Chemical Engineering Journal, vol. 166, No. 1 (Jan. 1, 2011), pp. 378-383.
Zhang et al. "Metal nanoclusters: New fluorescent probes for sensors and bioimaging," Nano Today, vol. 9, No. 1, (Feb. 1, 2014), pp. 132-157.
PCT International Search Report, PCT/EP2015/068193, dated Oct. 15, 2015.

\* cited by examiner

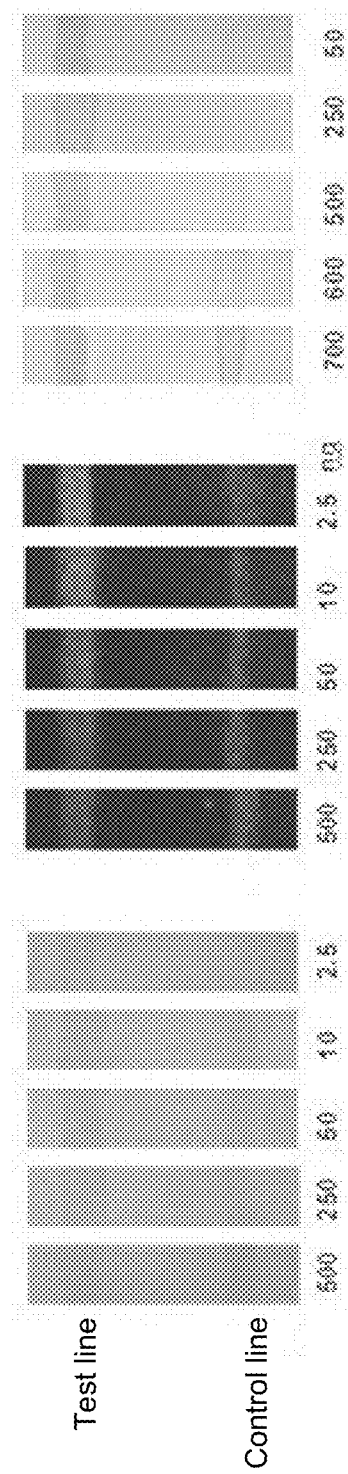

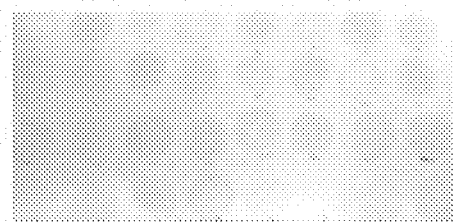
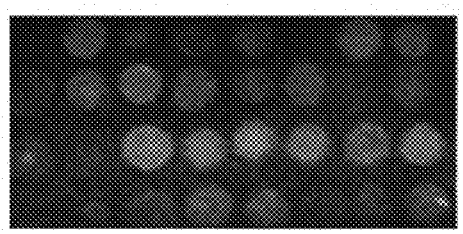
FIG. 4A  FIG. 4B
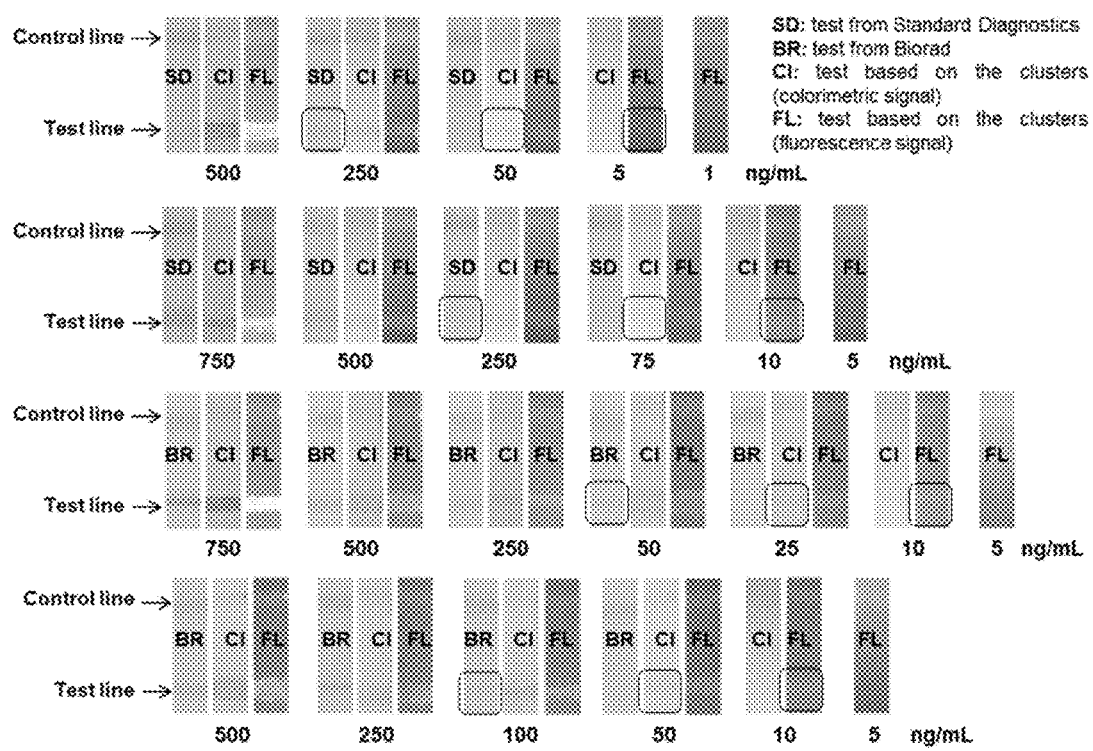
FIG. 5

CLUSTER FOR THE DETECTION OF AN ANALYTE

RELATED APPLICATIONS

This application is the National Phase of International Application No. PCT/EP2015/068193, filed Aug. 6, 2015, which designed the U.S. and that International Application was published under PCT Article 21(2) in English, which claims priority to European Patent Application No. 14180042.5, filed Aug. 6, 2014, all of which applications are expressly incorporated herein by reference in their entirety.

SEQUENCE LISTING

The instant application contains a Sequence Listing which has been submitted electronically in ASCII format and is hereby incorporated by reference in its entirety. Said ASCII copy, created on Aug. 14, 2019, is named Vossius-0449905_ST25.txt and is 604 bytes in size.

The present invention relates to a cluster for the detection of an analyte, said cluster comprising a plurality of visually detectable colored particles and a plurality of luminescent particles, wherein (i) the particles are bound to each other, and (ii) at least one binding partner of an analyte is bound to the colored particles and/or the luminescent particles.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Immunoassays are promising tools for the detection of pathogens, contaminants and other analytes with high specificity. Lateral flow immunoassays (LFIA) are especially interesting for applications requiring point-of-care (POC) assessment. LFIA is a mature technology and the fastest growing product sector in the diagnostic industry. The first commercial LFIA was produced in the 1990's, as a pregnancy test. Since then, the technology, its applications, and the industry have all continued to increase. As in 2006, over 200 companies worldwide were producing a range of testing formats, with a total value of approximately $2.1 billion dollars (USD) in major market segments (Won, R. C. and Tse, H. Y., In Lateral Flow Immunoassay, Springer, New York, 2009, p. 35.). LFIA provides low-cost and fast analysis without trained personnel for handling or expensive apparatus for reading (Posthuma-Trumpie, G. A., Korf, J., Amerongen, A., 2009. Anal. Bioanal. Chem. 393, 569-582). Due to these characteristics, LFIA is a good alternative for off laboratory or resource-poor settings. The test allows analysis in the field, providing real-time results and avoiding expensive sample transportation and long waiting times for results (Bai, Y. et al., 2012. RSC Advances 2, 1778-1781.). The application of the technology has expanded well beyond clinical diagnostics to areas as diverse as veterinary, agriculture, bio-warfare, food, environmental health and safety, industrial testing, as well as newer areas such as molecular diagnostics and theranostics. Most of LFIA follows the same principle. When the sample is added, the analyte and label are subjected to chromatography-like migration through a membrane, driven by capillary forces, and a result is read at the site of an immobilized capture reagent. Patents and publications about LFIA show variations of this principle and component structures, changing the sample pad (where sample preparation takes place), conjugate release pad (containing labels), bioreactors (trapping contaminants/interferents), reaction membrane (where are immobilized capture reagents) and absorbent pad (wick).

The conventional LFIA employs colloidal gold (Gandhi, S. et al., 2009. Biosens. Bioelectron. 25, 502-505; and Zhang, D. et al. 2011. Biosens. Bioelectron. 26, 2877-2882.), dyes (Ho, J. A. A. et al., 2008. Anal. Bioanal. Chem. 391, 479-485) or latex beads (Takanashi, S. et al., 2008. J. Virol. Methods 148, 1-8.) as labels to generate visual signals. A review indicates that 75% of LFIA have gold nanoparticles as labels for the detection of pathogen agents and chemical contaminants, followed by carbon black 4.2%, luminescent particles 4.2% and others (Ngom, B. et al., 2010. Anal. Bioanal. Chem. 397, 1113-1135). Colloidal gold-based test strips, in particular, have been produced commercially in large amounts for a variety of applications (Bai, Y. et al. 2012. RSC Advances 2, 1778-1781). However, the applicability of LFIA is limited when low concentration of analyte should be detected, such as in early diagnosis of diseases like Dengue fever (DF). DF results from viral infection transmitted by *Aedes aegypti*, a species of mosquito with a global distribution, which estimated affects 100 million of people every year, with 500 thousand cases of dengue hemorrhagic fever (DHF). For DHF, early medical care can save lives, decreasing mortality rates from more than 20% to less than 1% (Allwinn, R., 2011. Med. Microbiol. Immunol., 200, 155-159). Sensitivity limitations of LFIA persist on commercial systems and reduce their applications, as exemplified for 8 commercial kits for DF based on IgG/IgM detection (Blacksell S. D. J. Biomed. Biotechnol. 2012, 1-12). From all kits, only one showed the necessary specificity (97.6%) and sensitivity (65.3%) to be considered of clinical use (>50%). It means that only one test had the proportion of actual positives correctly identified (sensitivity) higher than 50% and the proportion of negatives correctly identified (specificity) higher than 50%. The need for tests with improved detection limit is not only highlighted for DF, but also for commercially available point-of-care tests for other diseases (Fu, E et al. 2011. Anal. Chem. 83, 7941-7946), such as *Chlamydia* (van Dommelen, L. et al., 2010. Sex. Transm. Infect. 86, 355-359; Vasoo, S. et al., 2009. Clin. Infect. Dis. 49, 1090-1093; and Skidmore, S. 2010. Sex. Transm. Infect. 86, 330) and influenza (Vasoo, S. et al., 2009. Clin. Infect. Dis. 49, 1090-1093; Drexler et al., 2009 Emerging Infect. Dis. 15, 1662-1664).

Fluorescent immunoassays are a promising alternative to conventional colorimetric detection methods due to their enhanced sensitivity (Linares, E. M. et al., 2013, Biosens. Bioelectron. 41, 180-185.). Recently a work developed by Khreich and co-authors (Khreich, N. et al., 2008. Anal. Biochem. 377, 182-188.) evaluated different labels (colloidal gold, fluorescent microsphere, dextrane rhodamine, dye microsphere and liposomes) for *Staphylococcus aureus* enterotoxin B (SEB) detection. Colorimetric labels allowed the detection of SEB at a concentration as low as 0.5 ng/mL. Colloidal gold showed a twice higher sensitivity as dye microspheres. On the other hand, fluorescent microspheres showed better sensitivity than either colorimetric label, resulting in a strong increase in sensitivity with a detection limit being close to a concentration of 0.02 ng/mL.

Although fluorescent labels generally provide lower detection limit, they require the use of fluorescence readers, which is contrary to the concept of a simple assay for impoverished environments. Therefore, there have been several attempts trying to enhance the sensitivity of fast immunoassays based on visible signal. Horton and colleagues (Horton, J. K. et al., 1991. Immunol. Methods 140, 131-134, and Kalogianni, D. Petal., 2011. Anal. Bioanal. Chem. 400, 1145-1152.) reported a 100-fold reduction of the detection limit via the immersion of a lateral flow strip into a silver enhancement solution. Reports include improvements in the detection limit of approximately 10-fold, using an enzymatic amplification system (Parolo, C. Et al., 2012. Biosens. Bioelectron., in press). However, in these studies, the user was still required to perform numerous steps, limiting the format appropriateness for use at the point of care.

As can be taken from the prior art discussion herein above, there is an ongoing need for a test format that is at the same time simple to perform and confers the required sensitivity for the early diagnosis of a variety of diseases, such as DF. This need is addressed by the present invention.

The present invention therefore relates in a first embodiment to a cluster for the detection of an analyte, said cluster comprising a plurality of visually detectable colored particles and a plurality of luminescent particles, wherein (i) the particles are bound to each other, and (ii) at least one binding partner of an analyte is bound to the colored particles and/or the luminescent particles.

A cluster is in general terms a group of compounds that are in close proximity. In accordance with the invention these compounds are visually detectable colored particles, luminescent particles and at least one binding partner of an analyte. As will be further detailed herein below, these compounds are bound to each other in the cluster of the invention. The cluster of the invention preferably does not comprise a coating, wherein a coating is a non-monolayer of one or more substances spreading over the complete surface of the cluster. It is, in particular, preferred that the surface of the cluster comprises at least some of the visually detectable colored particles, wherein the visually detectable colored particles preferably comprise or consist of metal and/or metal oxide and/or do not contain in their composition organometallic structures. More preferably, the surface of the cluster comprises both at least some of the visually detectable colored particles and at least some of the luminescent particles.

An analyte is a chemical substance that is the subject of an analysis, i.e. in accordance with the invention the detection of the analyte. The analyte may be selected, for example, from amino acid sequences (including protein or peptide), nucleic acid molecules (including DNA and RNA), lipids (including, for example, cell membrane lipids, lipopolysaccharides, cholesterol and retinol), and sugars (including, for example, mono-, di-, oligo-, polysaccharides or sugar portions of glycosylated proteins or peptides).

The analyte is in general present within a liquid sample. A sample is a limited quantity of a source being of considerably larger amount. The sample is intended to be similar to and to represent the source. The liquid sample is preferably a biological liquid sample, such as a sample obtained from a water source (e.g. sewage water), soil, plant or an animal. The liquid sample is preferably obtained from an animal. Animal samples may be obtained from tissue or a body fluid, such as amniotic fluid, aqueous humor and vitreous humor, bile, blood or blood serum, breast milk, cerebrospinal fluid, cerumen (earwax), chyle, chyme, endolymph and perilymph, exudates, feces, gastric acid, gastric juice, lymph, mucus, pericardial fluid, peritoneal fluid, pleural fluid, pus, rheum, saliva, sebum (skin oil), semen, sputum, synovial fluid, tears, sweat, vaginal secretion, vomit and urine. The animal is preferably human. Analytes in biological samples are frequently measured in the art for medical and research purposes.

An analyte may be quantitatively or qualitatively detected. Qualitative detection determines the presence or absence of an analyte, while quantitative detection determines the amount of the analyte in a sample. Quantification may be achieved, for example, by using competitive detection methods, wherein an unlabeled analyte in a sample competes with a labeled analyte to bind a binding partner. The amount of labeled, unbound analyte is then measured. The more analyte in the sample, the more labeled analyte gets competed off and hence the amount of labelled, unbound analyte is proportional to the amount of unlabelled analyte in the sample. Alternatively, calibrator samples may be used for quantification. Calibrator samples are known to contain a given concentration of the analyte to be detected. Comparison of detection results employing one or more calibrator samples to real sample detection makes it possible to interpret the signal strength in terms of the presence or concentration of the analyte in the sample.

A particle is a small localized object to which physical or chemical properties such as volume or mass can be ascribed. In accordance with the invention the particle has a maximum diameter of 1000 nm, preferably 750 nm, more preferably 500 nm and even more preferably 250 nm, and most preferably 200 nm. The minimal diameter is 1 nm, preferably 2 nm, more preferably 5 nm, and even more preferably 10 nm, and most preferably 20 nm. Consequently, the particles are with increasing preference in the size range of 1 nm to 1000 nm, 2 nm to 750 nm, 5 nm to 500 nm, 10 nm to 250 nm, and 20 nm to 200 nm. Due to their size the particles are also designated herein as "nanoparticles". It has to be understood that the sizes of the visually detectable colored particle and the luminescent particle can be chosen independently. It is, in particular, preferred that the visually detectable colored particles have a diameter of at least 20 nm, preferably of at least 30 nm and more preferably of at least 40 nm.

A visually detectable colored particle is a particle having a color in the visible spectrum of humans. The visible spectrum is the portion of the electromagnetic spectrum that is visible to the human eye. The human eye typically responds to wavelengths in the range of about 390 to 700 nm. The color of the particle is determined by the color of the light leaving the particle's surface. In this respect it is emphasized that the visually detectable colored particle per se—visual detectability being a property being immanent to the particle—has a color in the visible spectrum of humans (even though a single colored particle may be too small to be visible by the naked eye). The luminescent particle of the invention displays its color when present in the context of the cluster of the invention. The formation of the cluster does not substantially interfere with the color. Moreover, no additional steps for inducing the visibility of the color of the visually detectable colored particle are required. This preferably means that the particle displays its color under white light, such as sun light or equivalent artificial white light. The visually detectable colored particle of the invention can be simply observed by visual inspection in the context of the intact cluster, for example, during the methods of the invention described in detail herein below. In particular, no excitation of atoms within the visually detectable colored particle of the invention is required in order to generate a visually detectable color. For instance, no excitation by UV-light (i.e. below 380 nm) and/or infrared (IR)-light (i.e. above 700 nm) is required. WO 2007/070115 describes luminescent metallic cluster particles and uses thereof.

These luminescent metallic cluster particles emit light in the visible spectrum only upon photo-induced excitation, noting that excitation is by UV-light. Such luminescent metallic cluster particles and any other particles which require additional steps for inducing the particles' color—including the luminescent particle of the invention detailed herein below—have to be held distinct from the visually detectable colored particle of the present invention.

It is therefore preferred that the visually detectable colored particle of the invention has no luminescent properties. In other words, it is preferred that the visually detectable colored particle does not emit light as the result of the excitation of atoms within the particle by light and more preferably by any energy other than heat.

It may be required that several detectable colored particles are in close proximity and/or co-localize, such that a human can actually see the color of the visually detectable colored particle of the invention. It is therefore preferable that the visually detectable colored particles of the invention in the context of the cluster of the invention are visible to the naked human eye (i.e. without any magnification instruments, such as a magnifying glass, binocular or microscope).

A luminescent particle emits light as the result of the excitation of atoms within the particle by energy other than heat; usually light. This is in contrast to light emitted from incandescent bodies, such as burning wood or coal, molten iron, and wire heated by an electric current. The luminescent particle of the invention has the capability of emitting light as the result of the excitation of atoms within the particle by energy other than heat; usually light, when being present in the context of the cluster of the invention. The formation of the cluster does not substantially interfere with the luminescent properties of the luminescent particle. The luminescence of the luminescent particle of the invention can be induced in the context of the intact cluster, for example, during the methods of the invention described in detail herein below. Since also the luminescent particle of the invention is usually and preferably a nanoparticle, it may likewise be required that several detectable colored particles are in close proximity and/or co-localize, such that the luminescence becomes detectable either by instrumentation or the naked human eye. Luminescence may be caused by chemical, biochemical, or crystallographic changes, the motions of subatomic particles, or radiation-induced excitation of an atomic system. Luminescence is in accordance with present invention preferably photoluminescence. A photoluminescent particle emits light after the absorption of photons (electromagnetic radiation). Fluorescence is photoluminescence as a result of singlet-singlet electronic relaxation and phosphorescence, photoluminescence as a result of triplet-singlet electronic relaxation (typical lifetime: milliseconds to hours). Fluorescence and phosphorescence are preferred modes of luminescence in accordance with the present invention and will be further detailed herein below.

The luminescent particles may be glass or polymer particles being functionalized with a luminescent dye. Regarding the polymer, all kinds of polymers, which are able to incorporate dye molecules can be used. For this purpose the luminescent particles may be coated with a molecule (for example, surfactants) being luminescent or being able to incorporate a luminescent dye. Non-limiting examples of suitable polymers that can be used for the preparation of polymer particles are cyclodextrin-containing polymers, in particular cationic cyclodextrin-containing polymers, poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) (jointly referred to herein as "polyacrylic acids"), and copolymers and mixtures thereof, polydioxanone and its copolymers, polyhydroxyalkanoates, polypropylene fumarate), polyoxymethylene, poloxamers, poly(ortho)esters, poly(butyric acid), poly(valeric acid), poly(lactide-co-caprolactone), trimethylene carbonate, polyvinylpyrrolidone, polyorthoesters, polyphosphazenes, and polyphosphoesters. The polymer particles are preferably polystyrene particles.

Regarding the luminescent dye it is noted that several dyes, their properties and possible applications thereof are known in the art (see, for example, the database fluorophores.org). Depending on the application and desired properties of the luminescent particles and the cluster of the invention, the skilled person can select a suitable luminescent dye.

Instead of using particles which are functionalized with a luminescent dye, particles being itself a luminescent dye may be used. Non-limiting examples are fluorescent nanocrystals (also called quantum dots). Fluorescent nanocrystals are made of semiconductor materials that are small enough to display quantum mechanical properties, specifically its excitons are confined in all three spatial dimensions. Excitation and emission of the quantum dot are tunable by changing the size of the nanocrystals. Emission frequencies increase as the size of the nanocrystals decreases, resulting in a color shift from red to blue in the light emitted.

The particles are chemically bound to each other in accordance with the present invention. A chemical bond is an attraction between atoms that allows the formation of chemical substances that contain two or more atoms. The bond is caused by the electrostatic force of attraction between opposite charges, either between electrons and nuclei, or as the result of a dipole attraction. The strength of chemical bonds varies considerably; there are "strong bonds" such as covalent or ionic bonds and "weak bonds" such as dipole-dipole interactions, the London dispersion force and hydrogen bonding. The bonds between the particles are preferably "strong bonds". The particles may either be directly bound to each other by using functional groups of the particles or indirectly by third compounds. Means and methods for indirect binding of the particles will be further detailed herein below.

Within the cluster the particles are bound to each other in accordance with the present invention. That is, within the cluster each particle has to be bound to at least one other particle, such that the plurality of all particles forms a continuous cluster. As long as this prerequisite is met, it is not necessary that within the cluster each visually detectable colored particle is bound to a luminescent particle, or each visually detectable colored particle is bound to a visually detectable colored particle, or each luminescent particle is bound to a luminescent particle. Within the cluster the particles are preferably randomly bound to each other.

However, the particles may also be bound such as to form a certain pattern. For example, a cluster having the visually detectable colored particles in one portion of the cluster and the luminescent particle in the other portion of the cluster is also encompassed by the present invention. In this case, in the one portion each visually detectable colored particle is bound to a visually detectable colored particle, and in the other portion each luminescent particle is bound to a luminescent particle. Only at the boundary surface of the two portions the visually detectable colored particles are bound to luminescent particles. The portions of the cluster harboring the visually detectable colored particles and the luminescent particles, respectively, may or may not be of equal size. The ratio of the portion harboring the visually detectable colored particles to the portion harboring the luminescent particles is preferably 50:50 to 80:20, more preferably of 60:40 to 80:20, even more preferably 70:30 to 80:20 and most preferably about 80:20 by weight %.

A cluster may also have a concentration difference or a concentration gradient having an increased concentration of luminescent particles towards one end of the cluster while having an increased concentration of visually detectable colored particles towards the other end of the cluster. In case of a concentration difference, one portion of the cluster may, for example, show a ratio of visually detectable colored particles to luminescent particles of about 50:50 by weight % while a second portion shows a ratio of visually detectable colored particles to luminescent particles of about 80:20 by weight %.

The clusters may also comprise two or more, such as 3, 4 or 5, portions, each of said portions harboring only the visually detectable colored particles, or harboring only the luminescent particles, or harboring both the visually detectable colored particles and the luminescent particles at a certain ratio to each other. Said ratio may be independently selected for each portion. Further, the different portions may be randomly bound to each other or again such that a certain pattern is formed, e.g. by alternating portions harboring the visually detectable colored particles and portions harboring the luminescent particles.

The colored particles and/or the luminescent particles are also bound to at least one binding partner of an analyte in accordance with the present invention. Hence, the binding partner of an analyte may only be bound to the colored particles, or may be only bound to the luminescent particles, or may be bound to both the colored particles and the luminescent particles. In the above-discussed embodiments, wherein the cluster comprises two or more, such as 3, 4 or 5, portions, it may be decided separately for each portion, whether the binding partner of an analyte is only bound to the colored particles, or is only bound to the luminescent particles, or is bound to both the colored particles and the luminescent particles. Also the bond between the particles and the binding partner of an analyte is a chemical bond as defined herein above. In another alternative, visually detectable colored and luminescent particles alternate in the cluster. Other format in which the visually detectable colored and luminescent particles are ordered, are within the ordinary skills and fall within the claimed invention.

The binding partner of the analyte may be any molecule being capable of forming an attractive interaction with the analyte, said interaction resulting in a stable association in which the analyte and binding partner are close to each other. The binding partner of the analyte preferably specifically binds to the analyte. The attractive bonding between the analyte and its binding partner is in general weaker than a covalent bond. Examples of binding partners are described herein below.

The term "a plurality of particles" means in its broadest sense at least two particles and with increasing preference at least 3, at least 4, at least 5, at least 6, at least 7, at least 8, at least 9 and at least 10 particles. The term "a plurality of particles" likewise specifies with increasing preference upper-limits of up to 50 particles, up to 40 particles, up to 30 particles and up to 20 particles. The indicated minimum and maximum number of particles within a plurality of particles can be freely combined. For example, the term "a plurality of particles" means with increasing preference at least 2 and up to 50 particles, at least 4 and up to 40 particles, at least 5 and up to 30 particles and at least 6 and up to 20 particles. Since the term "a plurality of particles" means in its broadest sense at least two particles it follows that the cluster of the invention has to comprise at least two visually detectable colored particles and at least two luminescent particles. Thus clusters, wherein only one visually detectable colored particle and/or only one luminescent particle is present do not fall under the present invention. For example, Draz el al. (2012), ACS Nano, 6(9):7634-7643 describes a hybrid nanocluster plasmonic resonator for the detection of Hepatitis B virus, which comprises one central quantum dot and a few gold nanoparticles bound thereto. The nanocluster of Draz el al. (2012) is therefore structurally distinct from the cluster of the present invention. Moreover, the cluster of Draz el al. (2012) is functionally distinct from the cluster of the present invention, because it decomposes in the presence of the analyte Hepatitis B virus. The quantum dot is only luminescent in this decomposed state, in which state it is not in connection with the gold nanoparticles. The gold nanoparticles quench the luminescene of the central quantum dot in the intact nanocluster. The intact nanocluster described in Draz el al. (2012) is thus not luminescent.

The present invention describes novel clusters constituted by two types of particles, namely visually detectable colored particles (which are in accordance with the examples of the invention preferably gold particles) and luminescent particles (which are in accordance with the examples preferably fluorescent particles). The novel clusters provide an enhanced level of detection of an analyte by visual detection of the color, because the colored particles are concentrated in a cluster. The clustering increases the signal strength of the color thereby enhancing the detection limit of the analyte as compared to a single colored particle as well as a plurality of unconnected, single colored particles, comprised e.g. in a solution. Comparable to the colored particles, the cluster also concentrates the luminescent particles, thereby increasing the luminescence emission signal. This set up allows for the improvement of the detection limit in comparison to current tests, which employ a single luminescent particle as well as a plurality of unconnected, single luminescent particles, comprised e.g. in a solution.

The signal and analyte detection sensitivity are also enhanced by combining colored particles with luminescent particles. The presence of the analyte, being bound to the cluster of the invention, can be firstly determined by visual color inspection, i.e. the detection of the color of the colored particles of the cluster of the invention by eye. Detection of color and thus detection of test results by eye is advantageous, because no equipment apart from the human eye is needed. However, the downside is that the detection limit of the human eye is limited and therefore low concentration of an analyte, being bound to the cluster of the invention, may no longer be detected by eye.

The detection of the luminescence is optional. In case the analyte is already detected by eye, the step of the detection by luminescence may not be necessary. Yet, in order to balance the downside of visual color inspection (generated, e.g., by problems of judgment by visual inspection), the presence of the analyte can be in addition determined by detecting the luminescent particles of the cluster of the invention. This in particular done if the visual color is only slightly positive, thereby providing an uncertain result, or if the visual color is even not at all detectable. The luminescent particles have to be excited by light. For instance, a ultraviolet (UV) lamp or light emitted diode (LED) can be used to excite the luminescent particles which will then emit the detectable luminescent signal. Hence, also the step of luminescence detection is simple and only inexpensive equipment is required. The detection limit of luminescence is superior to the detection limit of visual color inspection. A low detection limit is of particular importance if detecting the analyte in the sample is indicative of the presence of a disease (e.g. in blood sample obtained from a patient) or a contamination (e.g. in drinking water samples). A low detection limit allows for the detection of the disease or contamination at an early stage. As illustrated in the examples, a LFIA method based on clusters shows a visible signal up to an analyte concentration of 10 ng/mL, but under UV light, the detection limit achieves lower values, up to an analyte concentration of 2.5 ng/mL. Hence, the cluster of the invention is preferably capable to detect the analyte at concentration of 3.5 ng/mL to 1.5 ng/mL, more preferably at a concentration of 3.0 ng/mL to 2.0 ng/mL, and most preferably at a concentration of about 2.5 ng/mL.

The use of clusters formed by two different types of particles is described in the prior art. For example, Bai and co-authors (Bai, Y. et al., 2012. RSC Advances 2, 1778-1781.) bound CdTe quantum dots (QD) onto larger silica nanoparticles, which increased greatly the fluorescence intensity due to the QD accumulation. However, the silica particles were only used as a QD carrier to concentrate the labels and the detection was exclusively based on fluorescence. Bai and co-authors did not incorporate visually detectable colored particles into their clusters.

More recently, an immune-dipstick assay was developed by Tang and co-authors (Tang, D. et al., 2009. Biosens. Bioelectron. 25, 514-518.) for the fast screening of aflatoxin B2 (AFT B2) in food. The detector reagent consisted of magnetic nanogold microspheres (MnGMs) with nano-$Fe_2O_3$ particles as a core and gold nanoparticles as a shell, and was bio-functionalized with monoclonal anti-AFT B2 antibodies. Result showed that the cutoff detection value was 3 times lower than that of gold nanoparticles at 0.9 ng/mL AFT B2. However, the $Fe_2O_3$ nanoparticles act as a substrate for the assembly of gold nanoparticles and did not play a direct role in the signal intensification. Furthermore, the $Fe_2O_3$ nanoparticles have to be held distinct from the luminescent particles as present in the clusters of the invention.

According to a preferred embodiment of the invention the visually detectable colored particles are metal or metal oxide particles, preferably particles made of Au, Ag, Ni, Pt, Cd, Fe, Cu, their oxides or any combination thereof, and more preferably particles made of Au, Ag, Fe oxide or any combination thereof. In this respect it preferred that the metal or metal oxide particles of the invention do not comprise any organometallic complexes.

Metallic nanoparticles are widely utilized in biomedical sciences and engineering (see for review Mody et al. (2010), J Pharm Bioallied Sci.; 2(4): 282-289). Usually metallic nanoparticles are made from Au, Ag, Ni, Pt, Cd, Fe, Cu, their oxides or any combination thereof. By way of example, Au, Ag and Fe oxide nanoparticles will be further described below.

In a preferred example the metal particles are gold nanoparticles (also known as colloidal gold). Colloidal gold particles are currently used in high technology applications such as organic photovoltaics, sensory probes, therapeutic agents, drug delivery in biological and medical applications, electronic conductors and catalysis. The optical and electronic properties of gold nanoparticles are tunable by changing the size, shape, surface chemistry, or aggregation state. In more detail, gold nanoparticles interaction with light is strongly dictated by their environment, size and physical dimensions. Oscillating electric fields of a light ray propagating near a colloidal nanoparticle interact with the free electrons causing a concerted oscillation of electron charge that is in resonance with the frequency of visible light. These resonant oscillations are known as surface plasmons. For small (~30 nm) monodisperse gold nanoparticles the surface plasmon resonance phenomona causes an absorption of light in the blue-green portion of the spectrum (~450 nm) while red light (~700 nm) is reflected, yielding a rich red color. As particle size increases, the wavelength of surface plasmon resonance related absorption shifts to longer, redder wavelengths. Red light is then absorbed, and blue light is reflected, yielding solutions with a pale blue or purple color. The surface plasmon resonance can be tuned by varying the size or shape of the nanoparticles, leading to particles with tailored optical properties for different applications. Hence, depending on their size gold nanoparticles are either intense red (for particles less than 100 nm or blue/purple (for larger particles). Gold nanoparticles of different size (diameter of 5 nm to 400 nm) are commercially available, for example, from Invitrogen. Also silver nanoparticles may be used. When 60 nm silver nanoparticles are illuminated with white light they appear bright blue. The bright blue color is due to a surface plasmon resonance that is peaked at a 450 nm wavelength. A unique property of silver nanoparticles is that this SPR peak wavelength can be tuned from 400 nm (violet light) to 530 nm (green light) by changing the particle size and the local refractive index near the particle surface. Also AuAg bimetallic nanoparticles are used in the art.

Due to their size, magnetic properties, and biocompatibility, superparamagnetic metal oxide ($Fe_xO_x$) nanoparticles have emerged as promising candidates for various biomedical applications, such as enhanced resolution contrast agents for MRI, targeted drug delivery and imaging, hyperthermia, gene therapy, stem cell tracking, molecular/cellular tracking, magnetic separation technologies (e.g., rapid DNA sequencing) early detection of inflammatory, cancer, diabetes, and atherosclerosis (see Mody et al. (2010), J Pharm Bioallied Sci.; 2(4): 282-289). The iron oxide nanoparticle is preferably an iron (II/III) oxide nanoparticle. Iron (II/III) oxide ($Fe_3O_4$) is the most magnetic of all the naturally occurring minerals and also one of the three main oxides of iron, while the other two oxids are FeO and $Fe_2O_3$.

In accordance with a further preferred embodiment of the invention, the luminescent particles are fluorescent particles or phosphorescent particles.

In connection with the preferred luminescent particles of the invention, any organic or inorganic dye, which shows fluorescent or phosphorescent properties can be used.

Fluorescence is the emission of light by a substance that has absorbed light or other electromagnetic radiation. Fluorescent dyes which may be used in connection with the present invention include but are not limited to FluoSpheres, Alexa Fluor Dyes, Atto Fluor dyes, FAM Fluor dyes, Cy3, Cy3.5, Cy5, Cy 5.5, FITC, AMCA, fluorescin, rhodamine, TAMRA. In most cases, the emitted light has a longer wavelength, and therefore lower energy, than the absorbed radiation. However, when the absorbed electromagnetic radiation is intense, it is possible for one electron to absorb two photons; this two-photon absorption can lead to emission of radiation having a shorter wavelength than the absorbed radiation. The emitted radiation may also be of the same wavelength as the absorbed radiation, termed "resonance fluorescence". Many analytical procedures involve the use of a fluorometer (i.e. a device being used to measure parameters of fluorescence, in particular wavelength and intensity), usually with a single exciting wavelength and single detection wavelength. Because of the sensitivity that the method affords, fluorescent molecule concentrations as low as 1 part per trillion can be measured. Fluorescence analysis can be orders of magnitude more sensitive than other techniques.

The most preferred fluorescence occurs when the absorbed radiation is in the ultraviolet region of the spectrum being invisible to the human eye, while the emitted light is in the visible region. In this case a simple UV lamp/LED can be used to excite the fluorescent dyes.

Unlike fluorescence, a phosphorescent material does not immediately re-emit the radiation it absorbs. The slower time scales of the re-emission are associated with "forbidden" energy state transitions in quantum mechanics. As these transitions occur very slowly in certain materials, absorbed radiation may be re-emitted at a lower intensity for up to several hours after the original excitation. In simple terms, phosphorescence is a process in which energy absorbed by a substance is released relatively slowly in the form of light.

In accordance with a preferred embodiment of the invention, the bonds between the particles are covalent bonds, preferably peptide bonds.

A covalent bond is a chemical bond that involves the sharing of electron pairs between atoms. A peptide bond (amide bond) is a covalent chemical bond formed between two molecules when the carboxyl group of one molecule reacts with the amino group of the other molecule, causing the release of a molecule of water ($H_2O$). Hence, the process is a dehydration synthesis reaction (also known as a condensation reaction), and usually occurs between amino acids. The resulting C(O)NH bond is called a peptide bond, and the resulting molecule is an amide. The four-atom functional group —C(=O)NH— is called a peptide link. Polypeptides and proteins are chains of amino acids held together by peptide bonds.

In accordance with the examples herein below the particles of the invention are linked within the cluster of the invention by peptide bonds. In order to establish these peptide bonds the visually detectable colored particles and the luminescent particles are coated with albumin and the formation of peptide bonds between the albumin molecules is initiated. Hence, the peptide bonding between the particles is preferably achieved by coating the particles with a protein and/or peptide and then linking the protein and/or peptides to each other. This is a particular example of indirectly binding the particles of the invention together to form the cluster, because the particles are not directly bound to each other but via a third bound being a protein and/or peptide coating the particles.

In accordance with another preferred embodiment of the invention the binding partner is selected from the group of a protein, such as an antibody, a DNA, a RNA, and an aptamer, such as a SPIEGELMER® (i.e., an L-ribonucleic acid aptamer (L-RNA aptamer)).

The skilled person can select a suitable binding partner based on the analyte to be detected.

The term "antibody" as used in accordance with the present invention comprises, for example, polyclonal or monoclonal antibodies. Furthermore, also derivatives or fragments thereof, which still retain the binding specificity, are comprised in the term "antibody". Antibody fragments or derivatives comprise, inter alia, Fab or Fab' fragments, Fd, F(ab')$_2$, Fv or scFv fragments, single domain $V_H$ or V-like domains, such as VhH or V-NAR-domains, as well as multimeric formats such as minibodies, diabodies, tribodies, tetrabodies or chemically conjugated Fab'-multimers (see, for example, Altshuler et al., 2010., Holliger and Hudson, 2005). The term "antibody" also includes embodiments such as chimeric (human constant domain, non-human variable domain), single chain and humanized (human antibody with the exception of non-human CDRs) antibodies. Various techniques for the production of antibodies and fragments thereof are well known in the art and described, e.g. in Altshuler et al., 2010. Thus, polyclonal antibodies can be obtained from the blood of an animal following immunisation with an antigen in mixture with additives and adjuvants and monoclonal antibodies can be produced by any technique which provides antibodies produced by continuous cell line cultures. Examples for such techniques are described, e.g. Harlow and Lane (1988) and (1999) and include the hybridoma technique originally described by Köhler and Milstein, 1975, the trioma technique, the human B-cell hybridoma technique (see e.g. Kozbor, 1983; Li et al., 2006) and the EBV-hybridoma technique to produce human monoclonal antibodies (Cole et al., 1985). Furthermore, recombinant antibodies may be obtained from monoclonal antibodies or can be prepared de novo using various display methods such as phage, ribosomal, mRNA, or cell display. A suitable system for the expression of the recombinant (humanized) antibodies or fragments thereof may be selected from, for example, bacteria, yeast, insects, mammalian cell lines or transgenic animals or plants (see, e.g., U.S. Pat. No. 6,080,560; Holliger and Hudson, 2005). Further, techniques described for the production of single chain antibodies (see, inter alia, U.S. Pat. No. 4,946,778) can be adapted to produce single chain antibodies specific for the target of this invention. Surface plasmon resonance as employed in the BIAcore system can be used to increase the efficiency of phage antibodies. Antibodies can be raised against amino acid sequences (in this case an amino acid epitope), nucleic acid molecules (e.g. against dsDNA), lipids (e.g. against phosphoinositides), and sugars (e.g. against sialylated poly-N-acetyllactosaminyl sugar chains). Hence, antibodies can be used to detect a wide range of analytes. The antibody is in accordance with the present invention preferably a monoclonal antibody.

An antibody specifically binds to a respective antigen. An antigen comprises at least one epitope. Proteinaceous or peptidic antigens are composed of an amino acid sequence. An epitope (also known as antigenic determinant) is the part of an antigen that is recognized by the antibody. Proteinaceous or peptidic epitopes are divided into two categories, conformational epitopes (discontinues stretch of amino acids) and linear epitopes (continues stretch of amino acids), based on their structure and interaction with the antibody.

Binding partners can be used to detect a wide range of analytes, including other amino acid sequences (which may be detected, e.g., by growth-fact binding proteins or SH2 or 3 domain-containing proteins) nucleic acid molecules (which may be detected, e.g., by RNA- or DNA-binding proteins; such as Poly-A binding protein or transcription factor), lipids (which may be detected, e.g., by lipopolysaccharide-binding proteins or fatty acid-binding proteins), sugars (which may be detected, e.g., by maltose-binding proteins), or small organic compounds (which may be detected, e.g., by calcium-binding protein, iron-binding protein, or folate-binding protein). Binding partners also include peptidomimetics. A peptidomimetic is a small protein-like chain designed to mimic a peptide. They typically arise either from modification of an existing peptide, or by designing similar systems that mimic peptides, such as peptoids and β-peptides. Irrespective of the approach, the altered chemical structure is designed to advantageously adjust the molecular properties such as, stability or biological activity. This can have a role in the development of drug-like compounds from existing peptides. These modifications involve changes to the peptide that will not occur naturally (such as altered backbones and the incorporation of non-natural amino acids).

The DNA or RNA is preferably an antisense nucleic acid molecule. The term "antisense nucleic acid molecule" is known in the art and refers to a nucleic acid which is complementary to a nucleic acid molecule representing a coding region. An antisense molecule according to the invention is capable of interacting with, more specifically hybridizing with the coding target nucleic acid. By formation of the hybrid, transcription of the target gene(s) and/or translation of the target mRNA is reduced or blocked. Standard methods relating to antisense technology have been described (see, e.g., Melani et al., Cancer Res. (1991) 51:2897-2901).

Aptamers are oligonucleic acid (DNA or RNA) or peptide molecules that bind a specific target molecule. Aptamers are usually selected from a large random artificial sequence pool, but natural aptamers also exist in riboswitches. Aptamers can be used for both basic research and clinical purposes as macromolecular drugs. Peptide aptamers consist of a short variable peptide domain, attached at both ends to a protein scaffold. They are designed to interfere with other protein interactions inside cells. Their double structural constraint greatly increases the binding affinity of the peptide aptamer to levels comparable to an antibody's (nanomolar range). The variable loop length is typically comprised of 10 to 20 amino acids, and the scaffold may be any protein which has good solubility properties. Currently, the bacterial protein Thioredoxin-A is the most often used scaffold protein, the variable loop being inserted within the reducing active site, which is a -Cys-Gly-Pro-Cys (SEQ ID NO:1)- loop in the wild protein, the two cysteine lateral chains being able to form a disulfide bridge. Peptide aptamer selection can be made using different systems, but the most used is currently the yeast two-hybrid system. Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers offer the utility for biotechnological and therapeutic applications as they offer molecular recognition properties that rival those of the commonly used biomolecules with a specific binding capacity, in particular antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications.

Aptamers are generally built using natural oligonucleotides. A SPIEGELMER® as a specific class of aptamers is built using L-ribose being the enantiomers of natural oligonucleotides. Like other aptamers, a SPIEGELMER® is able to bind molecules such as peptides, proteins, and substances of low molecular weight. As compared to normal aptamers, a SPIEGELMER® has a high stability in blood serum, since it is less susceptible to being cleaved hydrolytically by enzymes. Unlike other aptamers, a SPIEGELMER® is not directly made using SELEX (systematic evolution of ligands by exponential enrichment), as L-nucleic acids are not amenable to enzymatic methods, such as PCR, used in SELEX. Therefore, the selection is done with mirrored target molecules.

In accordance with a preferred embodiment of the invention the binding partner is an antibody, and the analyte is a proteinaceous or peptidic antigen.

In the example herein below the antibody is a monoclonal antibody against the NS1 glycoprotein of the Dengue fever virus, and the antigen is an antigen of the NS1 glycoprotein of the Dengue fever virus.

In accordance with a more preferred embodiment of the invention the binding partner is an antibody against a protein of the Dengue Virus, and the analyte is an antigen of said protein.

The Dengue fever virus genome codes for for the three structural proteins, capsid protein C, membrane protein M, envelope protein E, and the seven nonstructural proteins, NS1, NS2a, NS2b, NS3, NS4a, NS4b, NS5. In connection with the above embodiment the protein of the Dengue Virus is preferably selected from the seven nonstructural proteins.

In accordance with an even more preferred embodiment of the invention the binding partner is an antibody against the NS1 glycoprotein of the Dengue fever virus, and the analyte is an antigen of the NS1 glycoprotein of the Dengue fever virus.

According to a preferred embodiment of the invention the cluster has a diameter of 1 nm to 20 μm, preferably of 10 nm to 10 μm, more preferably of 20 nm to 1 μm and most preferably 50 nm to 500 nm.

As will be discussed herein below, the cluster of the invention is particularly useful when applied in a lateral flow immunoassay (LFIA). In particular, for applying the clusters in a lateral flow immunoassay it is advantageous that the diameter of clusters is within the ranges indicated in the above preferred embodiment, said diameters allowing that clusters can smoothly flow along the immunoassay. The skilled person is moreover well aware that the diameter of the cluster will also depend on the particle composition and size.

According to another preferred embodiment of the invention, a plurality of said clusters has an average diameter of less than 10 µm, preferably of less than 1 µm, more preferably of less than 500 nm and most preferably of less than 250 nm.

Also these average diameters, overlapping with the ranges indicated above, allow that the majority of the clusters can smoothly flow along the immunoassay, in particular an LFIA. The diameter ranges and the average diameter values may also be combined. Thus a plurality of said clusters may have, for example, an average diameter of less than 10 µm, wherein each cluster of the plurality of clusters has a diameter of 1 nm to 20 µm; preferably an average diameter of less than 1 µm, wherein each cluster of the plurality of clusters has a diameter of less than 10 nm to 10 µm; and more preferably an average diameter of less than 250 nm, wherein each cluster of the plurality of clusters has a diameter of 50 nm to 500 nm.

According to another preferred embodiment of the invention, the particles within the cluster have a diameter of 1 µm to 1 nm, preferably of 500 nm to 10 nm, more preferably of 100 nm to 20 nm and most preferably of about 40 nm.

The diameter ranges may be independently selected for the visually detectable colored particles and the luminescent particles. Thus, the visually detectable colored particles within the cluster may have a diameter of 1 µm to 1 nm, preferably of 500 nm to 10 nm, more preferably of 100 nm to 20 nm and most preferably of about 40 nm. Likewise, the luminescent particles within the cluster may have a diameter of 1 µm to 1 nm, preferably of 500 nm to 10 nm, more preferably of 100 nm to 20 nm and most preferably of about 40 nm.

Using particles having these diameter ranges allows for the generation of clusters having sufficient numbers of visually detectable colored particles and luminescent particles which allow for the detection of an analyte by visually detecting the color and by detecting the luminescence.

In accordance with a further preferred embodiment of the invention the ratio of visually detectable colored particles to luminescent particles is 50:50 to 80:20, preferably of 60:40 to 80:20, more preferably 70:30 to 80:20 and most preferably about 80:20 by weight %.

In connection with this preferred embodiment the term "about" means with increasing preference ±5 weight %, ±4 weight %, ±3 weight %, ±2 weight % and ±1 weight %. The clusters used in the examples herein below consist of 80 weight % visually detectable colored particles and 20 weight % luminescent particles and therefore the ratio about 80:20 by weight % is most preferred. As mentioned, the visual detection of the color is less sensitive then the determination of luminescence. Keeping the ratio of visually detectable colored particles to luminescent particles within the given ratios is particularly advantageous for ensuring that the color as well as the luminescence can be detected, if the analyte is present.

In accordance with a still further preferred embodiment of the invention the particles are coated with an agent having functionalities that allow binding the particles together.

The particles may have a surface which cannot or can only unsatisfactorily bind together. In such a case the particles are coated with an agent having functionalities that allow binding the particles together. The visually detectable colored particles and the luminescent particles may be coated with the same agent or different agents, as long as the agent(s) have functionalities that allow binding the particles together. Further, only the visually detectable colored particles or the luminescent particles may have to be coated with an agent having functionalities that allow binding the particles together.

The term "functionality" designates any residue allowing the formation of a chemical bond between the particles. Non-limiting examples of such functionalities are the residues —Na$^+$, —Cl$^-$, —NH$_2$, —COOH, —N$_3$, —C≡CH, —NHS, and —SH. The functionalities are preferably —NHS and —SH residues which allow binding the particles together by peptide bonds.

An agent having functionalities that allow binding the particles together may be a protein, a polysaccharide, or a linear or branched polymer, whereby proteins are most preferred. Suitable proteins comprise but are not limited to albumin and casein. The use of albumin is preferred. Suitable saccharides comprise but are not limited to chitosan and dextran. Suitable linear or branched polymers comprise but are not limited to polyethylene glycol.

The present invention also relates to a device for the detection of an analyte in a liquid sample, said device comprising a plurality of clusters according to the invention, wherein said device preferably comprises a solid phase having a sample site, wherein at the sample site the plurality of clusters is disposed.

The plurality of clusters determines a number of clusters being sufficient to detect the analyte. For this purpose in general an excess number of cluster is used in order to ensure that all analyte potentially be present in the liquid sample can be detected. The term "a plurality of clusters" means in its broadest sense at least two particles and with increasing preference at least 5, at least 10, at least 20, at least 50. The number of clusters designated by the term "a plurality of clusters" of course also depends on the type of device. In case the device is a LFIA device, a spot assay or a nitrocellulose membrane-based device the plurality of clusters is with increasing preference at least $5\times10^5$, at least $5\times10^6$, at least $5\times10^7$ and at least $5\times10^8$ clusters.

The plurality of clusters is preferably dried on the device, either by freeze drying of by air drying. Freeze-drying, also known as lyophilisation, lyophilization, or cryodesiccation, is a dehydration process typically used to preserve a perishable material or make the material more convenient for transport. Freeze-drying works by freezing the material and then reducing the surrounding pressure to allow the frozen water in the material to sublimate directly from the solid phase to the gas phase.

The liquid sample is preferably a solution and more preferably an aqueous liquid sample. An aqueous solution is a sample in which at least one of the solvents is water. When used in clinical diagnostics the sample may be, for example, urine, saliva, serum, plasma, whole blood, feces, or exudates (from wounds or lesions). When used for non-clinical applications the sample may be, for example, derived from soils, dust, vegetation, or food, or environmental swabs such as from food processing plants.

The format of the device of the invention is not particularly limited. The device may be, for example, in a suspension format, wherein the plurality of clusters according to the invention is suspended in the liquid sample. In this case the device may be a chamber harboring the liquid sample with the plurality of clusters suspended therein. However, it is preferred that the device comprises a solid phase having a sample site, wherein at the sample site the plurality of clusters is disposed. The solid phase may be, for example, cellulose (and derivatives e.g., nitrocellulose, acetate cellulose etc), a polymer support, silica (glass), or a metallic surface. In case the sample site of the solid phase is a metallic surface the particles of the invention may be concentrated on the device by magnetic attraction. In case the sample site of the solid phase is cellulose the particles of the invention may be disposed on the device by drying.

The device comprising a solid phase may have any known format of a device for the detection of an analyte in a liquid sample, such as a lateral flow immunoassay (LFIA), an array, a spot assay, or column chromatographic devices.

An array (most notably a microarray) as used herein designates a 2D array on a solid substrate (usually a glass slide or silicon thin-film cell) that is capable to detect two or more different analytes in a sample preferably using high-throughput screening miniaturized, multiplexed and parallel processing and detection methods. Two or more different analytes are with increasing preference at least 5, at least 10, at least 50, at least 100, and least 500 and least 1000 different analytes. The concept of arrays was first introduced and illustrated in antibody microarrays in 1983 and hence is well-established in the art. The array of the invention preferably comprises a plurality of clusters according to the invention, wherein each different type of cluster is capable to detect a different type of analyte and each different type of cluster is immobilized at a distinct, non-overlapping site of the array. Hence, the number of different analytes is directly proportional to the number of different clusters.

A spot assay is a simple assay, wherein a plurality of clusters according to the invention is immobilized on a distinct spot of a solid phase, said solid phase being preferably a cellulose or cellulose-based membrane. In case the spot assay is used for the presence or absence of an analyte one spot on the solid phase may suffice. In case the spot assay is used for the detection of the concentration of an analyte, spots comprising different amounts of the clusters according to the invention may be present on the solid phase and/or different amounts of the liquid sample of the invention may be applied to the spots. A spot assay, namely an immunospot assay is exemplified in the examples (see also FIG. 4). Hence, the spot assay is preferably an immonspot assay. An immunoassay is a biochemical test that measures the presence or concentration of an analyte in the liquid through the use of an antibody or immunoglobulin as the binding partner of the analyte.

A column affinity chromatographic device is a device which can be used to isolate individual analytes from the liquid sample. In column affinity chromatography, the stationary phase, being an adsorbent, is placed in a vertical column, usually a glass column. Silica gel ($SiO_2$) and alumina ($Al_2O_3$) are two solid adsorbents commonly used for column chromatography. In accordance with the invention, the stationary phase immobilizes the plurality of clusters according to the invention. The bond between the stationary phase and the cluster is preferably a covalent bond. The liquid sample (the mobile phase) to be analyzed by column chromatography is placed inside the top of the column and is passed through the column by gravity or by the application of air pressure. In case the analyte is present in the sample the analyte binds to the clusters being immobilized at the stationary phase, thereby separating an individual analyte from the liquid sample. An elution solvent is then placed inside the top of the column and is passed through the column by gravity or by the application of air pressure. The elution solvent dissolves the binding between the analyte and clusters. Suitable elution solvents are widely used in the art and, for example, separate the bonds between the clusters and the analyte by changing the pH and/or salt concentration. Thereby, the analyte is obtained in isolation. Column chromatography can be separated into two general categories, depending on how the solvent flows down the column. If the solvent is allowed to flow down the column by gravity, or percolation, it is called gravity column chromatography. If the solvent is forced down the column by positive air pressure, it is called flash chromatography. It is not clear the advantage of using the clusters in this application, because recognition molecules could be directly bound to the silica gel, for example. Maybe an interesting application would be the use of cluster (containing magnetica particles) for the enrichment of an analyte by magnetic filtration and detection by a second particle in the cluster (colorimetry, fluorescence etc).

The device of the invention is preferably in the format of a lateral flow immunoassay (see FIG. 1 for an example of a LFIA). A lateral flow immunoassay (LFIA) is also known as lateral flow tests, immunochromatographic strip (ICS) tests or simply strip-test in the art. They have been a popular platform for diagnostic tests since their introduction in the late 1980's. Lateral flow tests are used in the art for the specific qualitative or semi-quantitative detection of many analytes including antigens, antibodies, and even the products of nucleic acid amplification tests. One or several analytes can be tested for simultaneously on the same strip.

In a LIFA in accordance with the present invention first, the liquid sample is placed on the sample site of the strip, said site being in general at one end of the strip. The liquid sample may comprise or may be mixed with a buffer specific to the test. This buffer may simply be a diluent/running buffer or it may be much more complex and have specific components or properties required to make the LFIA perform properly, such as a cell lysis buffer. With the addition of the liquid sample, the plurality of clusters according to the invention is solubilized. When solubilized the clusters mix with and bind to the analyte in the sample, if the analyte is present in the sample. Then capillary action draws the fluid mixture from the sample site upstream into the solid phase, being in general a membrane. The sample/cluster molecule mix continues to move upstream the solid phase until it reaches a site with capture molecules being capable to bind to the analyte/cluster complex of the invention. It has to be understood that only the analyte/cluster complex of the invention is captured at the capture site. In case the analyte is not present in the sample the clusters are not bound. Only if the test for the analyte is positive, the color and/or luminescence of the clusters of the invention can be detected at the capture site. The capture site is in general close to the other end of the strip or at the other end of the strip, i.e. opposite to the end where the sample site is located.

Most LFIAs are intended to operate on a purely qualitative basis. However, it is possible to measure the intensity of the color and/or luminescence at the capture site to determine the quantity of an analyte in the liquid sample. Handheld diagnostic devices known in the art as lateral flow readers can be used to provide a fully quantitative assay result. By utilizing unique wavelengths of light for illumination in conjunction with either CMOS or CCD detection technology, a signal rich image can be produced of the actual capture site. Using image processing algorithms specifically designed for a particular test type and medium, line intensities can then be correlated with analyte concentrations. Alternative non-optical techniques are also able to report quantitative assays results. One such example is a magnetic immunoassay (MIA) which also allows for getting a quantified result.

A preferred device of the invention as defined herein above comprises a plurality of clusters according to the invention, and a solid phase having a sample site, wherein at the sample site the plurality of clusters is disposed. Hence, this device comprises a sample site and a solid phase.

A LFIA device on the other hand comprises at least the following three essential components: (i) A sample site, (ii) a solid phase and (iii) a capture site. Hence, a LIFA device comprises in addition to the components of this preferred device a capture site.

The sample site of a LFIA in general comprises a sample pad on which the liquid sample is loaded and a conjugate pad harboring the plurality of clusters according to the invention. The sample pad and the conjugate pad may be one pad (e.g. a pad of cellulose or glass fiber) or may be two different pads, wherein the conjugate pad is upstream of the sample pad and the two pads are positioned such that capillary flow communication between them is allowed. The sample pad may be made of cellulose, glass fiber or any other material which is able to mount and process the sample. The sample pad may in addition fulfill one or more of the following tasks: Modifying the pH of the sample, filtering out solid components from the sample, separating constituents of the sample, and adsorbing out unwanted components in the sample. Before the sample is applied on the sample pad, the pad is preferably pretreated by dipping it into a specific buffer containing a mix of a solution comprised of soluble proteins, surfactants/detergents, and other polymers. This pretreatment enhances steady flow and/or prevents nonspecific binding of sample components to the pad.

The conjugate pad may be made of a non-absorbent material such as fiberglass pad, polyester, rayon or a similar material. The conjugate pad is preferably of a synthetic material which ensures the efficient release of the clusters of the invention. The clusters according to the invention may be added to the conjugate pad, for example, by immersion or spraying. In immersion the conjugate pad is submerged in a suspension comprising the clusters. In spraying the pad is coated with clusters of the invention using, e.g., quantitative, directional aerosol dispense, being similar to an inkjet printer. Spraying is preferred because, the cluster application can be better controlled and dilution and washing away of any pad pretreatment (if present) is prevented.

The material of the solid phase is not particularly limited as long as the material provides sufficient analyte/cluster complex binding to enable the production of a sharp and intense signal at the capture site, while at the same time the level of nonspecific background is such that the result (i.e. the presence or absence of the analyte) can be bona fide interpreted. Suitable materials are porous cellulose or porous cellulose-based material, or sintered polymer. The solid phase is preferably a nitrocellulose (NC) membrane. So far, LFIA tests nitrocellulose is most abundantly used. The benefits of nitrocellulose are its low cost, capillary flow, high binding affinity for protein, ease of handling and cutting, as well as the ability of manufactures to varying thickness and components of the membrane to suit customer and market needs. Nitrocellulose is capable to bind proteins electrostatically through and interaction with the nitrate esters and the peptide bonds of the protein. The membranes' binding capacity can be determined by the skilled person based on the available surface area. This surface area is determined by pore size, porosity (pore density), membrane thickness, and unique physical characteristics of that particular polymer. These factors also affect capillary flow rate which can also dramatically affect a LFIA's overall performance. If a strip flows too fast sensitivity may be lost, and if it flows too slow specificity may be lost (e.g. increased background).

The solid phase may be treated with a blocking agent to prevent nonspecific binding of sample and clusters and to limit background signal along the membrane. Blocking may also be used to control flow rates and stabilize the test. The blocking process may involve immersion of the solid phase in an aqueous solution of proteins, surfactants, and/or polymers. After blocking the solid phase is in general dried.

In accordance with a further preferred embodiment the device additionally comprises a capture site, wherein at the capture site a plurality of capture agents binding to the analyte is immobilized, and wherein the capture site and the sample site are positioned such that capillary flow communication between the capture site and the sample site is allowed.

This device according to this preferred embodiment comprises the essential components of a LFIA and thus is a LFIA device.

The capture agents, being immobilized at the capture site, may be any molecule being capable of forming an attractive interaction with the analyte, thereby resulting in a stable association of the analyte with the capture site. The capture agents preferably specifically bind to the analyte. The attractive bonding between the analyte and the capture agent is in general weaker than a covalent bond. The capture agents have to be capable to bind the analyte when being present in the analyte/cluster complex. Hence, the capture agent shall not bind to a site of the analyte which is sterically blocked when bound to the cluster of the invention; i.e when bound to the binding partners of the analyte. The capture agents, though, may recognize a structure which is specific for the analyte/cluster complex. Hence, the capture site (or result site, or test site) comprises capture agents which are capable to bind to the analyte/cluster complex in the context of a LFIA. The analyte/cluster complex (if present) becomes immobilized at the capture site which is indicated by the color and/or luminescence of the cluster of the invention. The capture agents according to the invention may be added to the capture site, for example, by immersion or spraying which methods have been detailed herein above. The capture site is preferably in the form of a line.

The terms "capture agent" and "binding partner of the analyte" as used herein have to be held distinct. While both are capable of forming an attractive interaction with the analyte their place in the device is different. As discussed, the capture agents are immobilized at the capture site, while the binding partner of the analyte is bound to the visually detectable colored particles and/or luminescent particles and thus forms part of the clusters of the invention. The "capture agent" and "binding partner of the analyte" are preferably selected such that they do not compete for binding to the analyte. This may be achieved by selecting a capture agent which binds to a site of the analyte being different to the site recognized by the binding partner of the analyte.

Examples of binding partners of the analyte have been discussed in detail herein above in connection with the embodiments being directed to cluster of the invention. These binding partners of the analyte may likewise be used as capture agents to produce the capture site of the LFIA of the invention by immobilizing them at the capture site. A LFIA may have more than one capture site, thereby allowing capturing two or more analytes in parallel. In this case also the clusters of the invention in general comprise two or more different binding partners of analyte, each different binding partners of analyte being specific to a specific, distinct analyte.

WO 2009/152209 deals with the combination of visual and fluorescent detection methods for lateral flow immunoassay (LFIA). The sensitivity of visually read lateral flow immunoassay tests was enhanced by adding a small quantity of fluorescent dye or fluorescent latex particles to metal particles. However, the use of fluorescent particles and metal particles which are not bound to each other—as opposed to the two types of particles being bound together within the cluster of the invention—does not prevent the separate lateral flow of the two different types of particles (metal and latex) in a LFIA. It follows that the two different types of particles used as described in WO 2009/152209 do not arrive at the capture site of the LFIA at the same time.

By using the clusters of the invention, the LFIA shows enhanced signal intensity by concentrating the labels. Moreover, the results of the LFIA are more reproducible, because bounded particles avoid preferential interactions and different migration rates between the two different particle types. As is evident from the first embodiment of this invention, within the clusters of the invention the visually detectable colored particles and the luminescent particles are bound to each other. Hence, the cluster of the invention is a continuous structure comprising both the visually detectable colored particles and the luminescent particles. As discussed in greater detail herein above, in a LFIA capillary action draws the liquid sample comprising the clusters from the sample site upstream into the solid phase, until the clusters reach the capture site. The bonding between the two kinds of particles advantageously ensures that both particles flow in the context of the clusters at the same rate to the capture site. The bonding consequently ensures that the visually detectable colored particles and the luminescent particles reach the capture site at the same time. This in turn ensures that the results of visual color inspection and the detection of luminescence are very stable and reliable. The ratio of visually detectable colored particles and luminescent particles at the capture site reflects the ratio of visually detectable colored particles and luminescent particles in the cluster of the invention because in clusters the visually detectable colored particles and luminescent particles flow together to the capture site as a contiguous structure.

Thus, the present invention provides clusters, which allow enhancing the sensitivity and reproducibility of LFIA by concentrating colored and luminescent particles as a single structure to recognize an analyte molecule. The combination of such particles in clusters provides structures with improved properties in comparison to the current labels: double check signal (colorimetric and luminescent), easy flow avoiding differential migration of particles, and in addition multiple interaction points with higher surface area/label for the binding of the binding partners of the analyte to the cluster as compared to single particles.

It is furthermore preferred that a LFIA device of the invention comprises one or more of the optional components of a device as defined in the following preferred embodiments of the invention In accordance with a preferred embodiment of the invention, the device additionally comprises a control site, wherein at the control site a plurality of control agents binding to the clusters, preferably binding to the binding partner of the clusters are immobilized, and wherein the control site is positioned such that capillary flow communication between the sample site and the control site is allowed.

The control agent, being immobilized at the control site, may be any molecule being capable of forming an attractive interaction with the clusters, thereby resulting in a stable association of the clusters with the control site. While not strictly necessary, it is preferred that the LFIA incorporates a control site (which is preferably in the form of a line) upstream of the sample site which picks up the clusters of the invention which have not bound the analyte. These clusters are either excess clusters in case the analyte is present in the sample, or almost all clusters in case the analyte is not present in the sample. Hence, the control site has to comprise control agents being capable of specifically binding to the cluster of the invention. Importantly, the control agents do not substantially bind preferably do not bind to the analyte. In the simplest form such control agent may be the analyte per se, which is immobilized at the control site, or a fragment of the analyte still being recognized by the binding partner of the analyte, being present in the clusters of the invention. For example, in case the binding partner of an analyte within the cluster is an antibody the control agent being immobilized at the control site may be an antigen of the antibody or an Fc-Receptor. In this example, the immobilized antigen or Fc-Receptor is capable to form an attractive interaction with the antibody being present in the cluster of the invention, thereby resulting in a stable association of the clusters with the capture site. The control site confirms that the test has operated correctly. In case an analyte is present appearance of a color and/or luminescence at the capture site and optionally, in case of excess clusters which do not carry the analyte, also at the control site indicates the presence of the analyte in the sample, while a valid negative test produces a color and/or luminescence only at the control site.

According to a preferred embodiment of the invention, the device additionally comprises an absorbent pad which is positioned downstream of the flow path after the sample site, the capture site and, if present, the control site.

The absorbent pad is also called a wick or wicking pad in the art. The absorbent pad is advantageous in order to pull the liquid sample fluid off of the membrane and to allow the capillary flow of the membrane to keep flowing in the proper direction and at the proper rate. If no absorbent pad is used dependent on the solid phase which is used, the liquid sample (and optionally buffer) might flow down the membrane and could raise the background or possibly cause false positives. Absorbent pads may be made from non-woven, cellulose fiber sheets. These pads can be manufactured in a variety of thicknesses and densities to suit the needs of the device, in particular LFIA.

According to a further preferred embodiment of the invention, the device additionally comprises a backing card, preferably a paper or plastic-adhesive backing card.

Due to the delicate nature of the materials used in an LFIA, as well as the need to maintain a precise, direct contact between components to ensure proper reagent and sample flow, the device of the invention preferably comprises a backing card. Backing cards are usually pre-treated with pressure-sensitive adhesive selected for its stability in the assay and to insure it does not leach chemicals that may interfere with results. A related concern for manufacturers is that the adhesive is strong enough to properly bind the materials to the card but that it also does not flow too far into them and inhibit the capillary action by reducing the available bed volume. The adhesive card may initially be covered with a liner which may be pre-slit for easier assembly of test components. Many materials are available depending on the needs of the assay platform and manufacture configurations of the LFIA. The more common materials are plastic-adhesive backing card made of polystyrene, vinyl, polyester (clear or opaque), and/or Mylar.

According to a further preferred embodiment the invention, the device additionally comprises a laminate cover tape.

The Laminate Cover Tape is an adhesive tape that acts as a protective barrier and prevents evaporation of reagents and helps to limit back-flow of reagents. When using some particularly delicate materials a cover tape is essential to maintain integrity of the device, in particular LFIA device. The tape may have any number of designs imprinted upon it, such as test identification or trade names. The cover tape should be clear over the test and control line sections of the device. As with the "backing card", discussed above, a fine balance must be achieved between adhesive strength and migration of the adhesives to prevent assay interference and loss of bed-volume.

According to a further preferred embodiment the invention, the device additionally comprises a housing.

A housing is typically made of two pieces that snap together and protect the assembly of the device, in particular LFIA device. The device is contained within this housing that allows the unit to be handheld more easily and protects the device from damage and environmental contamination. In case of a LFIA device windows on the side of the housing allow for applying the liquid sample, and for detection of the color and/or luminescence at the capture site and, if present, the control site. At all sites this window may be a little hole in one half of the housing. The window may also be a clear plastic or glass window that protects the membrane from being accidentally damaged or splashed while still allowing visualization of these sites at the capture site and/or the control site.

The present invention also relates to a kit for the detection of an analyte comprising (i) the cluster of the invention, or the device according of the invention, and (ii) information and/or instructions how to use the kit.

The kit is intended to be used in the methods of the invention which will be further detailed herein below. Accordingly, the information and/or instructions how to use the kit preferably describe how to perform the methods of the invention.

The present invention furthermore relates to a method for the detection of an analyte in a liquid sample comprising (a) contacting the cluster of the invention, or the device of the invention with the liquid sample, and (b) determining the presence of the analyte by (i) visual color inspection, and optionally (ii) detection of luminescence.

As defined herein above, the cluster of the invention comprises a plurality of visually detectable colored particles and a plurality of luminescent particles. In accordance with this method the above-discussed advantage of having the option of detecting the analyte by visual color inspection, and detection of luminescence applies. For the detection of color by eye no equipment apart from the human eye is needed. In case no color is observed, lower concentration of the analyte may still be detected by the detection of luminescence.

The invention also relates to a method for the detection of an analyte in a liquid sample by a device of the invention, said device comprising a solid phase having a sample site, wherein at the sample site the plurality of clusters is disposed and a capture site, wherein at the capture site a plurality of binders to the analyte is immobilized, and wherein the capture site and the sample site are positioned such that capillary flow communication between the capture site and the sample site is allowed, said method comprising (a) contacting a liquid sample with the sample site, (b) allowing the liquid sample to flow to the capture site, (c) determining the presence of the analyte at the capture site by (i) visual color inspection, and optionally (ii) detection of luminescence.

The device used in accordance with this method comprises the essential feature of a LFIA, being (i) a sample site, (ii) a solid phase and (iii) a capture site as defined herein above. Hence, the device according to this method is a LFIA device. As discussed above, the clusters of the invention are particularly advantageous when used in a LFIA due to the fact that the visually detectable colored particles and the luminescent particles are bound together in the clusters of the invention.

In addition, also in accordance with this method the above-discussed advantage of having the option of detecting the analyte by visual color inspection, and detection of luminescence applies.

In accordance with a preferred embodiment of the above method the device additionally comprises a control site, wherein at the control site a plurality of binders to the clusters, preferably to the binding partner of the clusters is immobilized, and wherein the control site is positioned such that capillary flow communication between the sample site and the positive control is allowed, and the method further comprises (b') allowing the liquid sample to flow to the control site, and (c') determining the presence of the analyte at the control site by (i) visual color inspection, and optionally (ii) detection of luminescence.

The device used in accordance with this method comprises the three essential features of a LFIA and in addition a control site as defined herein above. Hence, also the device according to this method is a LFIA device. As discussed in greater detail herein above, the control site confirms that the test has operated correctly and therefore is preferably comprised in a LFIA-based method.

The figures show:

FIG. 1: Exemplary lateral flow immunoassay

FIG. 2A-2I: Transmission electron microscopy of clusters after separation. Bright field images of (FIG. 2A) gold nanoparticles, (FIG. 2B) polystyrene nanoparticles and (FIG. 2C) low energy loss spectra of gold and polystyrene nanoparticles. Bright field (FIG. 2D) and 25 eV energy loss (FIG. 2E) from the same area showing better resolution for polystyrene nanoparticles observation. Cluster images (FIG. 2E-FIG. 2G) at 25 eV of the fraction used in lateral flow tests and images (FIG. 2H and FIG. 2I) of the removed fraction of clusters.

FIG. 3A-3C: Lateral flow immunoassay for Dengue virus NS1 protein detection based on clusters (FIG. 3A) under UV light (FIG. 3B) and gold nanoparticles (FIG. 3C). The visible detection limits are shown by the red circles.

FIG. 4A-4B: Immunospot assay for Dengue fever detection based on clusters (FIG. 4A-4B). Right image was taken under UV light (FIG. 4B).

FIG. 5: Pictures of two serum dilution series for each commercial kits (Standard Diagnostics, SD, and Biorad, BR). Each concentration has pictures of the tests following the order: (1) commercial test, SD or BR, (2) colorimetric, CI, and (3) fluorescence, FI, signal of the cluster based test. The circles indicate the lowest concentration that the observers could recognize by naked eyes.

The examples illustrate the invention.

EXAMPLE 1- MATERIALS AND METHODS

In order to illustrate the invention, gold and fluorescent nanoparticle clusters were used to detect Dengue fever. A protein non-structural from the virus, NS1, was chosen as target analyte. The result was compared to gold based LFIA.

Chemicals

Gold nanoparticles (mean diameter: 40 nm), bovine serum albumin (BSA) powder, biotin, streptavidin, anti-streptavidin IgG antibody, N-(3-Dimethylaminopropyl)-N- ethylcarbodiimide hydrochloride (EDC), dialysis membranes (MWCO 100 kDa and 130 kDa), sucrose, potassium phosphate mono- and dibasic were purchased from Sigma-Aldrich (Milwaukee, USA). Streptavidin-labeled gold nanoparticles (mean diameter: 40 nm) was purchased from British Biocell (Cardiff, United Kingdom). FluoSpheres (PS) carboxylate-modified microspheres (excitation: 580 nm/emission: 605 nm) 0.04 µm, and nitrocellulose AC99 membrane were obtained from Invitrogen (Carlsbad, United States) and Whatman (Maidstone, United Kingdom), respectively. Sample and conjugate pad were obtained from Pall (Dreieich, Germany). Absorbent pad and backing card were provided from Millipore (Billerica, USA) and Lohmann (San Jose, USA), respectively. Dengue virus NS1 glycoprotein mouse monoclonal antibody (supernatant) and Melon gel IgG purification kit were obtained from Abcam (Cambridge, United Kingdom) and Thermo Scientific (Rockford, United States), respectively. Dengue NS1 Ag ELISA was purchased from Standard Diagnostics (Youngin, Korea).

Preparation of Gold- and Polystyrene-Nanoparticle Protein Conjugates

Gold nanoparticle dispersions at 15% were adjusted to pH 8 with NaOH 0.01M and 30 µL of an albumin solution at a concentration of 1 mg/mL was added to 0.3 mL of the gold dispersion. The mixture was stirred for 30 min, and then, to remove the excess of proteins, it was centrifuged at 5000 rpm for 15 min at 4° C. The clear supernatant was carefully removed, and the precipitated gold conjugates were resuspended in 400 µL of 0.01M phosphate buffer, pH 7.4, and stored at 4° C. Gold nanoparticles conjugated with NS1 antibody was produced by following the same procedure. Albumin coated polystyrene nanoparticles were prepared as described by Linares and coauthors (Linares, E. M. et al., 2013, Biosens. Bioelectron. 41, 180-185).

Preparation of Gold-Polystyrene Nanoparticle (PS) Clusters

Colloidal gold and fluorescent particles, previously coated with albumin, were covalently bound by forming peptide bonds between albumin molecules, using water-soluble carbodiimide to activate the surface carboxyl groups. To produce clusters with 80:20 (wt. %) of gold:PS, 300 µL of gold nanoparticles at 15% of solids was mixed with 562 µL of PS nanoparticles at 2% and incubated during 30 minutes in a shaker at RT. Subsequently, 2 mg of EDC (1-ethyl-3-(3-dimethylamino) propyl carbodiimide hydrochloride) was added to the suspension and incubated for 3 hours at RT. Thereafter, the suspension was centrifuged twice at 3000 rpm for 2 minutes and washed with 0.01 mol/L phosphate buffer, pH 7.4. Clusters were deposited on 1 mL of 1 mol/L sucrose solution in a centrifuge tube and centrifuged at 13000 rpm at 4° C. for 30 min. An aliquot of 100 µL was removed and the rest was divided in two aliquots. The aliquot on the top was used for the assay, after passing through a 220 µm filter.

Cluster Functionalization with Biomolecules

Clusters were conjugated to streptavidin and monoclonal NS1 Dengue antibody. An aliquot of 500 µL of cluster dispersion 80:20 gold:PS was added to 500 µL of a 0.5 mg/mL solution of protein dissolved in 0.01 mol/L phosphate buffer, pH 6. The suspension was incubated for 30 minutes at RT. Subsequently, 1 mg of EDC was added and mixed by vortexing and the pH were adjusted to 6.5 with diluted NaOH. The dispersion was incubated on a shaker for 3 hours at RT. To separate the protein-labeled clusters from unbound proteins, the suspension was centrifuged three times at 3000 rpm for 10 minutes at RT. The final suspension was kept in a phosphate buffer containing 1% BSA.

Strip Tests and Immunospot Assay

Before setting up the strip test for clusters, all used membranes received different treatments: the sample pad was dipped into 0.01 mol/L phosphate buffer, pH 7.4, containing with 5% BSA and 0.05% Tween20 and dried for 2 hour at 60° C.; the conjugate pad was previously immersed in 1 mmol/L borate buffer, pH 9, with 10% of sucrose, and then clusters at 5% (w/v) were deposited and dried at RT; anti-NS1 protein antibody and biotinylated-albumin at a concentration of 1 mg/mL in 0.01 mol/L phosphate buffer, pH 7.4, were spotted onto nitrocellulose to form the detection and control lines by using Dimatix printer from Fujifilm (Santa Clara, USA). BSA was biotinylated according to Guesdon, J. L. et al., 1979. J. Histochem. Cytochem. 27, 1131-1139. Ho, J. A. A., Zeng, S. C., Tseng, W. H., Lin, Y. J., Chen, C. H. 2008. Anal. Bioanal. Chem. 391, 479-485. The detection pad was dried at RT; and the absorbent pad was used as received. Subsequently, all membranes were laminated on the backing card with an overlap of 2 mm between them. The membranes were cut at 4 mm wide. Serum samples were analyzed by adding 100 µL on the sample pad. When the flow stopped, 100 µL of 0.01 mol/L phosphate buffer at pH 7.4 was added. The same buffer was used as blank. Analysis was performed after 25 min.

Immunospotting Assay

For mutiple tests, 4 µL of serum was deposited on the nitrocellulose membrane (7 cm×10 cm) with 15 mm spacing between each spot to avoid contamination and checking the alignment between them to fit on the wells of an ELISA microplate. This sample volume was the minimum volume necessary to observe a clear result. After 10 minutes, a blocking solution containing BSA 3% in phosphate buffer 0.01 mol/L, pH 7.4 was added to cover the entire membrane for 15 minutes at RT. Subsequently, the blocking solution was removed and 3 mL fluorescent conjugates 1% in phosphate buffer 0.01 mol/L, pH 7.4 was added and incubated for 30 minutes.

Comparison with Commercial Kits

Two kits, Standard Diagnostics Bioline Dengue Duo and Biorad Strip, were used to compare their performance with the proposed assay. The kits were chosen based on their performance described by Blacksell S. D. J. Biomed. Biotechnol. 2012, 1-12. Eight infected serum samples were diluted with phosphate buffer to produce solutions with lower NS1 concentration. The dilution varied with the initial concentrations of NS1, which were determined using enzyme linked immunosorbent assay. A panel of 14 observers analyzed the tests and verified the minimum dilution that could be observed by them. The visual detection limit was established by the concentration which at least half of the observers could detect. The tests were performed in duplicate and the observers could visualize the same signal in the strip tests with the same concentration. Pictures were recorded and the signals of the test lines (area: 1 mm×4 mm) were converted to gray scale and then compared with graphs of gray scale vs. NS1 concentration. The acquired images under UV lamp were converted to gray scale and the signal was inverted in the scale to facilitate the comparison with the colorimetric signal.

EXAMPLE 2-USE OF CLUSTERS OF THE INVENTION TO DETECT NS1

Cluster Characterization

Spectra from EELS (Electron energy loss spectroscopy) were obtained for gold (FIG. 2A) and polystyrene (FIG. 2B) nanoparticles from the areas indicated in the images and are depicted in the FIG. 1c. Polystyrene spectrum has higher intensity at the low energy loss than gold, and hence it will appear brighter in the energy image. The bright field (FIG. 1D) and its respective image at 25 eV (FIG. 2E) show clearer that polystyrene particles are poorly observed at bright field but better observed in the low energy loss image. The first fraction (from up to down in the centrifuge tube) concentrates smaller clusters as observed in the FIG. 2E-G, where it is possible to observe cluster up to 5 particles with mixed composition. The images from the second fraction indicate the presence of bigger clusters with variable composition and format. Tests with each fraction showed that the first fraction produces better signal and reproducibility.

Detection Limit for LFIA Based on the Clusters and Compared to Gold Nanoparticles LFIA based on clusters (FIG. 3A-B) shows a visible signal up to 10 ng/mL, but when the strip tests are under UV light, the detection limit achieves lower values, up to 2.5 ng/mL. In order to compare the clustering effect on the detection limit, LFIA based on gold nanoparticles were built and depicted in the FIG. 3C. It shows a visible test line until 500 ng/mL, once the signal at 250 ng/mL is barely observable. The results demonstrate that clusters provide a detection limit 50 times lower than gold nanoparticles and it decreases to 200 times under UV lamp.

Thus, if the colored sign is slightly positive, indicating uncertain result, a lamp/LED can be used to excite the fluorescent particles and the fluophores will emit in the visible spectrum. It will provide sensitivity 4 times better than the colorimetric signal.

Clusters Used to Detect NS1 in an Immunospotting Assay

A panel with 48 samples of Dengue infected patients was deposited on nitrocellulose and detected with gold-fluorescent nanoparticles cluster. FIG. 4 indicates that the fluorescent nanoparticles provide an additional signal that contributes to a more reliable assay. Based on the exposed results, nanoparticle clusters represent a powerful option to overcome sensitivity limitations of LFIA.

Comparison with Commercial Kits

FIG. 5 shows the comparison of the two kits with the proposed assay, showing the pictures for two serum dilutions per kit. FIG. 5 indicates the serum dilution series and the performance of the commercial kits in comparison to the cluster based test. The lowest concentrations indicated as visible by the observers are shown by the circles. The cluster based tests showed better performance than the commercial kits.

TABLE 1

Visual detection limits for the proposed method and the Biorad strip.

| | Detection limit (ng/mL) | | |
|---|---|---|---|
| | Biorad | Cluster | |
| | Colorimetry | Colorimetry | Fluorometry |
| Sample 1 | 50 | 25 | 10 |
| Sample 2 | 100 | 50 | 10 |
| Sample 3 | 100 | 50 | 25 |
| Sample 4 | 200 | 100 | 50 |

The detection limit obtained for the Biorad Strip is 200 ng/mL and the detection limit observed for the tests based on cluster is 100 ng/mL for the colorimetric signal and 50 ng/mL for the fluorometric signal.

The Biorad strip tests showed better performance than the Standard Diagnostics Bioline Dengue Duo, but it is has lower sensitivity than the tests based on the clusters.

Label Comparison with Other Labels for LFIA

Different labels for Dengue fever detection were compared. The results indicate that the cluster of particles shows better performance that the most used labels for LFIA or immunspotting assay.

TABLE 2

Comparison of labels for Dengue fever detection.

| Detection system | Assay type | Detection limit (ng/mL) | Duration (min) |
|---|---|---|---|
| Gold nanoparticles ("gold standard") | Lateral flow immunoassay | 500 | 20 |
| Carbon black | Lateral flow immunoassay | 10 | 25 |
| Fluorescent nanoparticles | Immunospotting assay | Optical fiber reader: 5 ELISA reader: 15 UV lamp: 200 | 45-60 |
| PhosphorescentPSHEMA-Ru particles | Immunospotting assay | Microscope: 190 | 25 |
| Gold-fluorescent nanoparticle clusters | Lateral flow immunoassay | Visible: 10 Under UV: 2.5 | 25 |

Optimization During Cluster Preparation

Numerous reactions were performed to develop and optimize the clusters, including the items:

Particle functionalization: It is preferred to avoid the direct immobilization of the streptavidin/antibody on the particle surface Spacer: the biofunctionalization is preferably enhanced by using a spacer based on BSA coating Cluster composition: depending on the specific application of the cluster of the invention, the composition of particles was optimized, e.g., by changing the particle concentration, reaction time and activator concentration in the production process of the clusters.

TABLE 3

Summary of the advantages of cluster based assays for Dengue fever detection.

| | Cluster | Gold nanoparticles (standard) |
|---|---|---|
| Colorimetric NS1 Detection limit (ng/mL) | 100 | 200-500 |
| Fluorescence NS1 Detection limit (ng/mL) | 50 | — |
| Capability to detect the disease from the outbreak of the symptoms (day) | $1^{st}$-$2^{nd}$ | $3^{rd}$ |
| Capacity to recognize the analyte | Enhanced by the highest number of available recognition molecules | Limited by the low number of recognition molecules immobilized on the particles (hindrance) |
| Capacity to determine the analyte in low concentration | Enhanced by fluorescence | Limited by the visual color provided by single colored particles |

The invention claimed is:

1. A cluster for the detection of an analyte, said cluster comprising:
   a plurality of visually detectable colored particles a plurality of luminescent particles, and at least one binding partner of an analyte, wherein
   (i) the visually detectable colored particles and the luminescent particles are covalently bound to each other through a covalent bond that is a peptide bond, wherein the convalent bond is a peptide bond,
   (ii) the binding partner of the analyte is bound to the colored particles, the luminescent particles, or both, and,
   (iii) the visually detectable colored particles are non-organometallic metal or metal oxide particles.

2. The cluster of claim 1, wherein the visually detectable colored particles are metal or metal oxide particles comprising Au, Ag, Ni, Pt, Cd, Fe, Cu, or an oxide thereof.

3. The cluster of claim 1, wherein the luminescent particles are fluorescent particles or phosphorescent particles.

4. The cluster of claim 1, wherein the at least one binding partner is selected from the group consisting of a protein, a DNA, a RNA, and an aptamer.

5. The cluster of claim 4, wherein the at least one binding partner is an antibody, and the analyte is a proteinaceous or peptidic antigen.

6. The cluster of claim 5, wherein the antibody is an antibody against the NS1 glycoprotein of the Dengue fever virus, and the proteinaceous or peptidic antigen is an antigen of the NS1 glycoprotein of the Dengue fever virus.

7. The cluster of claim 1, wherein the cluster has a diameter of 1 nm to 20 μm.

8. The cluster of claim 1, wherein a ratio of the visually detectable colored particles to the luminescent particles is 50:50 to 80:20 by weight %.

9. The cluster of claim 1, wherein the colored particles and the luminescent particles are coated with an agent having at least bifunctionalities that allows binding of the colored particles and the luminescent particles together.

10. A device for the detection of an analyte in a liquid sample, said device comprising a plurality of the clusters of claim 1, wherein said device comprises a solid phase having a sample site, wherein at the sample site the plurality of clusters is disposed.

11. The device of claim 10, wherein the device additionally comprises a capture site, wherein at the capture site a plurality of capture agents binding to the analyte are immobilized, and
   wherein the capture site and the sample site are positioned such that capillary flow communication between the sample site and the capture site is allowed.

12. A kit for the detection of an analyte comprising
   (i) the cluster of claim 1; and
   (ii) information and/or instructions describing how to use the kit.

13. A method for the detection of an analyte in a liquid sample comprising
   (a) contacting the cluster of claim 1 with the liquid sample, and
   (b) determining the presence of the analyte by
      (i) visual color inspection, and optionally
      (ii) detection of luminescence.

14. A method for the detection of an analyte in a liquid sample by the device of claim 11, said method comprising
   (a) providing the device of claim 11,
   (b) contacting a liquid sample with the sample site,
   (c) allowing the liquid sample to flow to the capture site, and
   (d) determining the presence of the analyte at the capture site by
      (i) visual color inspection, and optionally
      (ii) detection of luminescence.

15. The cluster of claim 4, wherein the at least one binding partner is an L-ribonucleic acid aptamer.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Peptide aptamer

<400> SEQUENCE: 1

Cys Gly Pro Cys
1
```